(12) United States Patent
McGaffigan

(10) Patent No.: US 7,771,424 B2
(45) Date of Patent: Aug. 10, 2010

(54) INTEGRATED METALIZED CERAMIC HEATING ELEMENT FOR USE IN A TISSUE CUTTING AND SEALING DEVICE

(75) Inventor: Thomas Haynes McGaffigan, Saratoga, CA (US)

(73) Assignee: Starion Instruments, Sunnyvale, CA (US)

( * ) Notice: Subject to any disclaimer, the term of this patent is extended or adjusted under 35 U.S.C. 154(b) by 807 days.

(21) Appl. No.: 11/080,479

(22) Filed: Mar. 16, 2005

(65) Prior Publication Data

US 2006/0212030 A1   Sep. 21, 2006

(51) Int. Cl.
A61B 18/12 (2006.01)
(52) U.S. Cl. ............... 606/51; 606/49; 606/52
(58) Field of Classification Search .......... 606/27, 606/49, 51
See application file for complete search history.

(56) References Cited

U.S. PATENT DOCUMENTS

| | | | |
|---|---|---|---|
| 3,768,482 A | 10/1973 | Shaw | |
| 4,161,950 A | 7/1979 | Doss et al. | |
| 4,714,189 A | 12/1987 | Tovey | |
| 4,850,353 A | 7/1989 | Stasz et al. | |
| 4,862,890 A | 9/1989 | Stasz et al. | |
| 4,958,539 A | 9/1990 | Stasz et al. | |
| 5,026,370 A * | 6/1991 | Lottick | 606/42 |
| 5,043,229 A | 8/1991 | Mizuhara | |
| 5,352,222 A | 10/1994 | Rydell | |
| 5,451,747 A * | 9/1995 | Sullivan et al. | 219/528 |
| 5,456,684 A | 10/1995 | Schmidt et al. | |
| 5,637,406 A | 6/1997 | Asai et al. | |
| 5,718,701 A * | 2/1998 | Shai et al. | 606/41 |
| 5,891,142 A * | 4/1999 | Eggers et al. | 606/51 |
| 5,893,846 A | 4/1999 | Bales et al. | |
| 5,925,039 A | 7/1999 | Landingham | |
| 6,132,429 A | 10/2000 | Baker | |
| 6,235,027 B1 | 5/2001 | Herzon | |
| 6,447,511 B1 | 9/2002 | Slatter | |
| 6,500,532 B1 | 12/2002 | Ruefer et al. | |
| 6,533,778 B2 | 3/2003 | Herzon | |
| 6,558,376 B2 | 5/2003 | Bishop | |
| 6,626,901 B1 | 9/2003 | Treat et al. | |
| 6,699,571 B1 | 3/2004 | Antalek | |
| 6,726,686 B2 * | 4/2004 | Buysse et al. | 606/51 |
| 6,905,497 B2 * | 6/2005 | Truckai et al. | 606/49 |
| 7,011,656 B2 | 3/2006 | McGaffigan et al. | |
| 7,025,065 B2 | 4/2006 | McGaffigan et al. | |
| 7,033,356 B2 * | 4/2006 | Latterell et al. | 606/48 |

(Continued)

FOREIGN PATENT DOCUMENTS

WO   2005/048863   6/2005

OTHER PUBLICATIONS

PCT International Search Report, Feb. 21, 2008.

*Primary Examiner*—Henry M Johnson, III
*Assistant Examiner*—Aaron Roane
(74) *Attorney, Agent, or Firm*—Greenblum & Bernstein, P.L.C.

(57) ABSTRACT

A tissue cutting and sealing device, having a pair of opposing elements dimensioned to grasp tissue therebetween; and a heating assembly on at least one of the opposing elements, wherein the heating assembly includes: a ceramic body; and a metalized portion extending along a top surface of the ceramic body. The top surface of the ceramic body preferably has a width greater than the metalized portion.

21 Claims, 4 Drawing Sheets

U.S. PATENT DOCUMENTS

| | | |
|---|---|---|
| 7,101,371 B2 * | 9/2006 | Dycus et al. .................. 606/49 |
| 7,160,298 B2 * | 1/2007 | Lawes et al. .................. 606/51 |
| 7,211,079 B2 | 5/2007 | Treat et al. |
| 2001/0014803 A1 | 8/2001 | Herzon |
| 2003/0069571 A1 | 4/2003 | Treat et al. |
| 2003/0125735 A1 | 7/2003 | Herzon |
| 2003/0129382 A1 | 7/2003 | Treat et al. |
| 2003/0195498 A1 | 10/2003 | Treat et al. |
| 2003/0220637 A1 * | 11/2003 | Truckai et al. ................ 606/28 |
| 2004/0073205 A1 | 4/2004 | Treat et al. |
| 2006/0142751 A1 | 6/2006 | Treat et al. |
| 2006/0212031 A1 | 9/2006 | McGaffigan et al. |
| 2007/0208330 A1 | 9/2007 | Treat et al. |
| 2008/0114349 A1 | 5/2008 | Treat et al. |
| 2009/0234347 A1 | 9/2009 | Treat et al. |

* cited by examiner

INTEGRATED METALIZED CERAMIC HEATING ELEMENT FOR USE IN A TISSUE CUTTING AND SEALING DEVICE

TECHNICAL FIELD

The present invention is related to surgical tissue cutting and sealing devices.

BACKGROUND OF THE INVENTION

Various surgical cutting blade systems exist that involve an electrically heated blade. Some of these cutting blade systems have a ceramic component with a metalized layer thereon. Examples are found in U.S. Pat. Nos. 3,768,482; 4,161,950; 4,850,353; 4,862,890; 4,958,539; and 5,925,039. In addition, various scissor-type cutting systems exist that involve a ceramic component and a metalized component. Examples are found in U.S. Pat. Nos. 5,352,222; 5,893,846; and 6,447,511. Unfortunately, the above systems all involve cutting tissue, and are not adapted to tissue sealing.

U.S. Pat. No. 5,456,684 describes a multifunction surgical device that can be used for cutting or cauterizing tissue, providing irrigation or for electrosurgery. Unfortunately, this device can not be used for both cutting and sealing tissue at the same time. Moreover, this device passes current through the tissue to provide cauterization.

U.S. Pat. Nos. 6,235,027 and 6,533,778 and U.S. Published Application Nos. 2001/0014803 and 2003/0125735 to Herzon all describe a thermal cautery forceps system. This system uses a pair of ceramic heaters having opposing flattened surfaces. These opposing flattened surfaces are brought together to pinch tissue therebetween. The ceramic heaters heat and squeeze the tissue to cauterize it. Specifically, Herzon describes a ceramic heater in which the ceramic is a semiconductor ceramic. (Being resistive, it generates heat when electrical current is passed through it). This semiconductor ceramic member has homogeneous resisitivity, and thus it generates heat uniformly across its surface. Because heating is uniform, there is only a sealing zone created if heated to sealing temperatures and only a cutting zone created if heated to cutting temperatures. As a result, the Herzon system can only be used to cauterize tissue, or to cut through tissue, but not both at the same time.

SUMMARY OF THE INVENTION

The present invention provides a tissue cutting and sealing device, having: a pair of opposing elements dimensioned to grasp tissue therebetween; and a heating assembly on at least one of the opposing elements. The heating assembly includes: a ceramic body; and a metalized portion extending along a top surface of the ceramic body. Preferably, the top surface of the ceramic body has a width greater than the metalized portion. In various embodiments, the opposing elements may be jaws or arms.

The metalized portion is preferably formed integral to the ceramic body by a brazing process.

An advantage of the present heater assembly is that it increases the amount of energy that can be delivered to a vessel being sealed as compared to previous designs. Moreover, the present heater assembly can provide a high watt density resistance heater device that is simultaneously able to apply pressure and heat energy to tissue to seal and divide the tissue.

In addition, the present ceramic heater assembly has increased thermal conductivity as compared to previous designs. This is advantageous in that it allows the heater assembly to have more uniform temperatures across its length and thickness, in spite of varying thermal loads along its length. Moreover, ceramics are inherently resistant to high temperatures, and are rugged at high temperatures. In addition, ceramics do not burn, smoke or outgas as do plastics.

Preferably as well, the ceramic body is dimensioned wide enough such that a tissue cutting zone forms adjacent to the metalized portion and a tissue sealing zone forms on either side of the cutting zone adjacent to a top surface of the ceramic body. As such, the cutting zone forms where the metalized portion directly contacts the tissue and sealing zones form where the ceramic body directly contacts the tissue.

Therefore, another advantage of the present heater assembly is that it increases the surface area at which heating is delivered to a vessel being sealed as compared to previous designs. Specifically, the present invention can both increase the resistance and the effective surface area of the heater at the same time as compared to previous "hot wire" designs.

The metalized portion is formed directly onto the top of the ceramic body and is thus raised with respect to the ceramic body. In preferred embodiments, the top surface of the ceramic body is curved such that the center of the ceramic body is raised with respect to the edges of the ceramic body. As a result, the metalized portion (disposed along the top center of the ceramic body) is also raised with respect to the edges of the ceramic body.

A further advantage of having a heating assembly formed from a metalized portion on top of a ceramic body (as compared to a solid wire sitting on top of a low temperature plastic) is that the resistance of the heater can be adjusted during fabrication to whatever resistance is required (by tailoring the metallization process used to form the heater). Thus, increases in both heater resistance and surface area can be achieved without sacrificing the required high watt density.

An advantage of the present system, therefore, is that its "cermet" (i.e. ceramic-metallic) heater configuration provides cutting and sealing zones of different temperatures due to its differently constructed zones of active (i.e. metallized portion) heater and its passive ceramic heat spreader. This particularly contrasts with the above discussed Herzon system which may either operate as a single large sealing zone, or a single large cutting zone, depending upon what temperature it is heated to.

In one embodiment, one of the opposing elements is moveable and the other of the opposing elements is stationary, and the heating assembly is mounted on the stationary opposing element. In this particular embodiment, the other (i.e.: moveable) element preferably comprises a compliant working surface for grasping tissue.

In various embodiments, the present heater assembly may be disposed on devices including a pair of surgical forceps or tweezers, or on various endoscopic devices.

When disposed on a pair of surgical forceps, the heating assembly may be disposed in an extended portion of the surgical forceps main body, with a pin passing through the distal end of the heating assembly. Such pin may be used to complete a circuit between the metalized portion and a the exterior of the surgical forceps main body. In optional embodiments, a bottom surface of the ceramic body may also be curved upwardly such that only the edges of the bottom surface of the ceramic body contact the extended portion of the surgical forceps main body. This design is very advantageous in preventing heat loss from the heater assembly into the main forceps body.

DETAILED DESCRIPTION OF THE DRAWINGS

Figure 1:
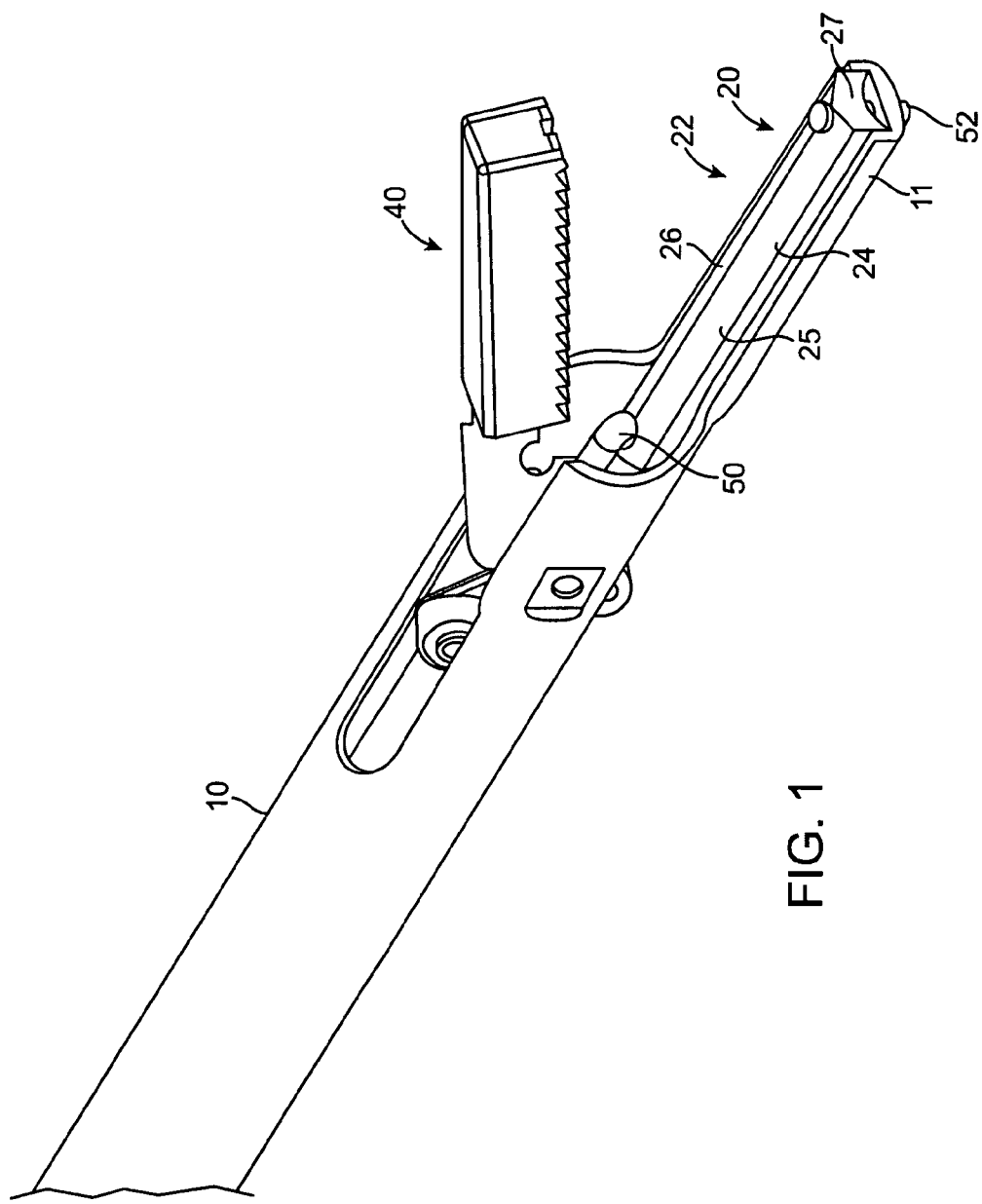
FIG. 1 is a perspective view of the present heater assembly at a distal end of a pair of surgical forceps.
Figure 2:
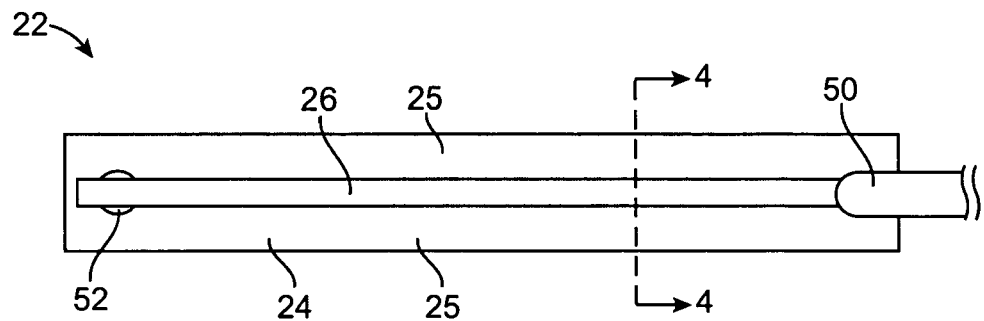
FIG. 2 is a top plan view of the heater assembly of FIG. 1.

FIGS. 1 to 4 illustrate a first embodiment of the present heater assembly positioned on a distal end of an endoscopic device used for tissue sealing and cutting pair of surgical forceps. FIG. 5 illustrates a second embodiment of the present heater assembly positioned on a surgical device, that may include a forceps or tweezers. It is to be understood that these examples are non-limiting and that the present heater assembly may be used on any other form of tissue cutting and sealing device.

Turning first to FIGS. 1 to 4, a tissue cutting and sealing device is provided on the distal end of an endoscopic device 10, as follows.

A pair of opposing jaws 20 and 40 dimensioned to grasp tissue therebetween are provided. A heating assembly 22 is provided on jaw 20. Heating assembly 22 includes a ceramic body 24 with a metalized portion 26 extending along a top surface of ceramic body 24. As can be seen most clearly in FIG. 4, the top surface 25 of ceramic body 24 has a width greater than metalized portion 26.

In accordance with various aspects of the present invention, the metalized portion 26 is formed integral to ceramic body 24. This may be accomplished by a metal brazing process. Conventional descriptions of systems of brazing a metalized portion of material directly onto a ceramic material are described in U.S. Pat. Nos. 4,714,189; 5,043,229; 5,637,406; and 6,699,571, and are incorporated herein by reference in their entirety.

In various embodiments, metalized portion 26 may be made from titanium, zirconium, niobium, vanadium, nickel or molybdenum. However, it is to be understood that the present invention is not so limited, and that other materials and processes of forming a metalized portion 26 directly onto the top of ceramic body 24 may be used.

Ceramic body 24 may optionally comprise zirconia or alumina, but is not so limited. In various embodiments, ceramic body 24 may be formed by a ceramic injection molding process, or by pressed ceramic molding. In addition, the ceramic body may be formed by flame spraying ceramic directly onto a steel (or other metallic) member.

Figure 4:
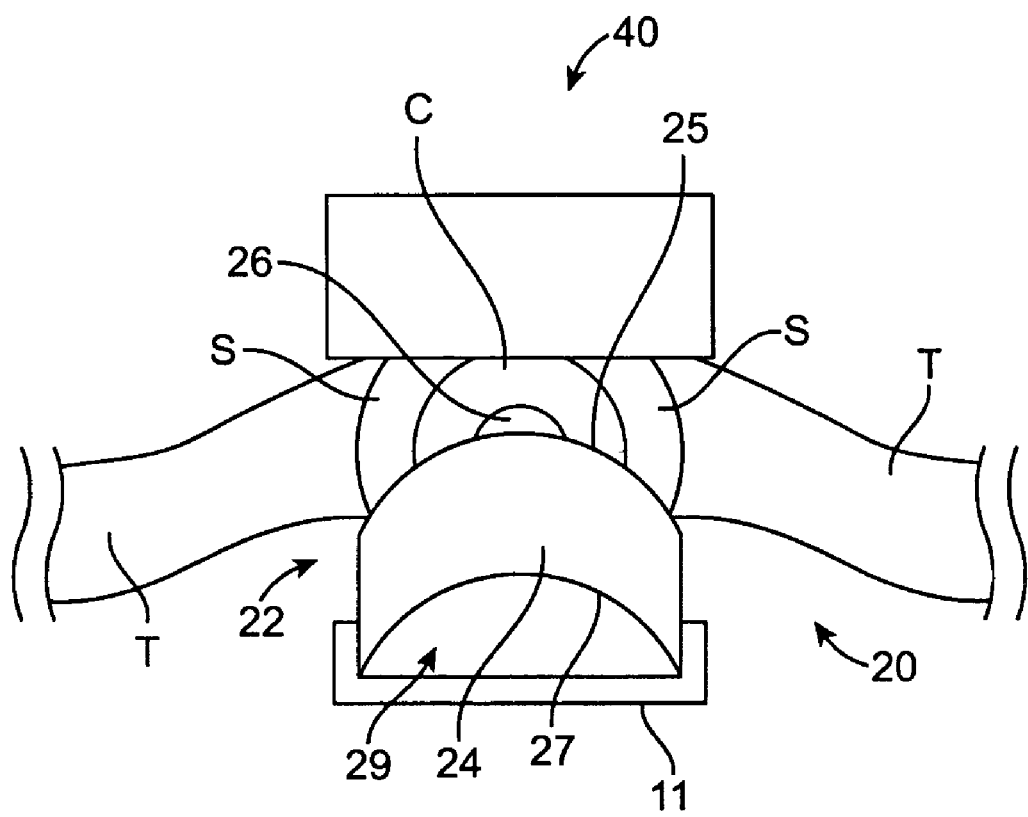
FIG. 4 is a front sectional view of the heater assembly of FIG. 1 in operation, taken along line 4-4 in FIGS. 2 and 3, showing a central tissue cutting zone with a tissue sealing zone on either side.
Figure 5:
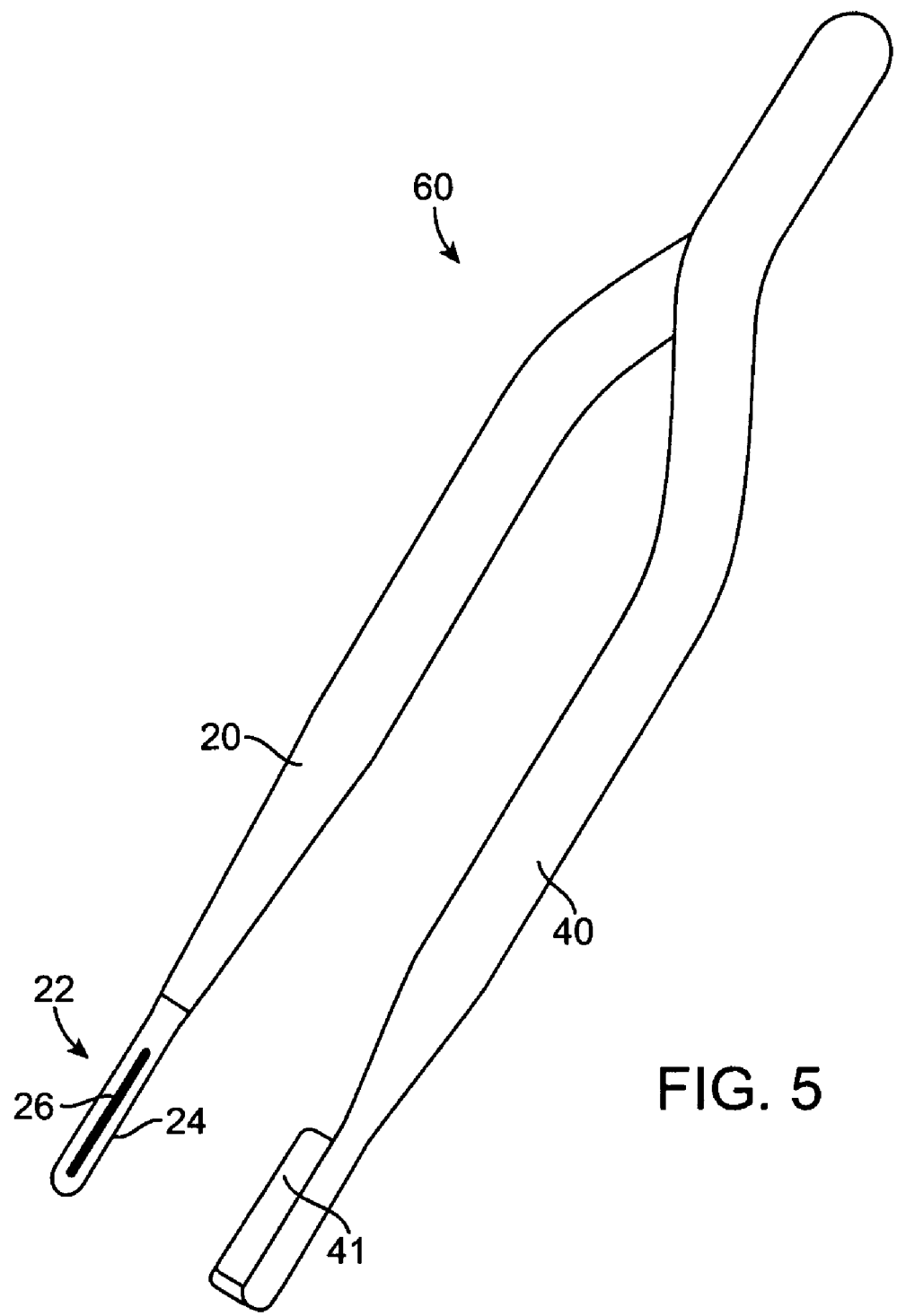
FIG. 5 is a perspective view of the present heater assembly on a pair of surgical tweezers.

As can be seen in FIG. 4, ceramic body 24 is dimensioned wide enough such that when tissue T is held therebetween, a tissue cutting zone C forms adjacent to metalized portion 26. A tissue sealing zone S forms on either side of cutting zone C. As can be seen, tissue sealing zones S form adjacent to a top surface 25 of ceramic body 24. Thus, cutting zone C forms where metalized portion 26 directly contacts tissue T and sealing zones S form where top surface 25 of ceramic body 24 directly contacts tissue T.

As can also be seen, top surface 25 of ceramic body 24 may be curved such that the center of ceramic body 24 is raised with respect to the edges of the ceramic body. Thus, when tissue T is grasped and squeezed between opposing jaws 20 and 40, the central portion of tissue T will be under greater pressure than the portions of tissue T towards the edges of the opposing jaws 20 and 40.

The heater assembly provides a resistive heating element 24 on top and integral with the ceramic substrate 22. This design is particularly advantageous in that the temperatures in ceramic body 24 are always lower than the temperatures in the metalized portion 26. In addition, the ceramic acts as a heat spreader that increases the effective seal area of the heater. As explained above, this design promotes tissue sealing adjacent to the ceramic (in tissue sealing zones S) and tissue cutting adjacent to the metalized portion (in tissue cutting zone C).

As a result, the present design is particularly advantageous in that the tissue T in cutting zone C will be subjected to both higher temperatures and higher pressures than the tissue T in sealing zones S. Thus, a combination of heat and pressure is used to cut the tissue, as follows.

The heat will be highest adjacent to metalized portion 26. In addition, the pressure on the tissue will be greatest in the area adjacent to metalized portion 26. This is due to two factors. First, metalized portion 26 is formed directly onto the top surface 25 of ceramic body 24. Metalized portion 26 thus sticks upwardly from top surface 25, as shown. Secondly, top surface 25 is curved upwardly at its center (i.e.: directly under metalized portion 26), further raising metalized portion 26 with respect to the edges of top surface 25 of ceramic body 25.

As can be seen in FIG. 1, opposing jaw 40 is moveable and opposing jaw 20 is stationary. Preferably, opposing jaw 40 may be covered with, or include, a compliant working surface for grasping tissue. Such compliant material may be silicone rubber, but is not so limited.

Figure 3:
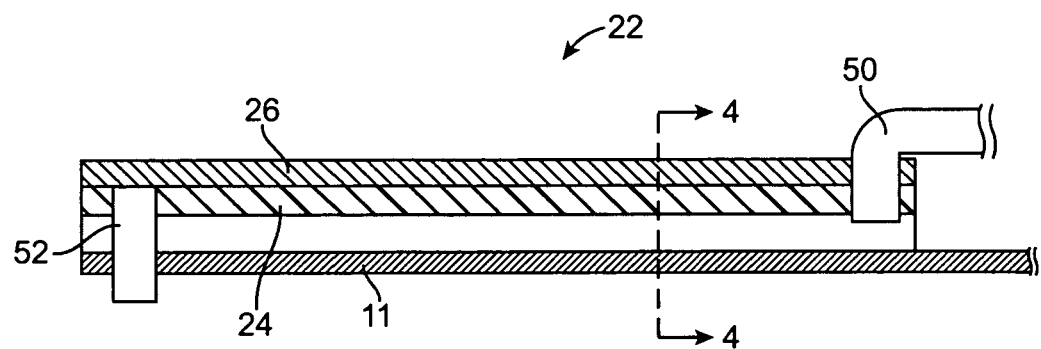
FIG. 3 is a sectional side elevation view of the heater assembly of FIG. 1.

As can be seen in FIGS. 1, 3 and 4, heating assembly 22 may be disposed in an extended distal portion 11 of the endoscopic device 10 main body. As can also be seen, the bottom surface 27 of ceramic body 24 may be curved upwardly such that only the edges of bottom surface 27 of ceramic body 24 contact the extended portion 11 of the endoscopic device main body 10. Thus, an air gap 29 is formed between bottom surface 27 of ceramic body 24. Air gap 29 prevents heat from being conducted away from heater assembly 22 and passing into extended distal portion 11 of the endoscopic device 10 main body.

In optional embodiments, metalized portion 26 may be used to complete a circuit between a power wire 50 and pin 52. Specifically, electricity passes from power wire 50, through metalized portion 26, through pin 52 and into extended portion 11 of the surgical forceps main body. An advantage of this design is that power wire 50 may be positioned to extend along through endoscopic device 10, with the outer metallic body (e.g.: extended portion 11) of endoscopic device 10 completing the circuit. The electricity passing through metalized portion 24 heats metalized portion 24. The electrical interconnections where wire 50 and pin 52 connect to heater assembly 22 may be brazed onto the ends of metalized portion 26 of ceramic body 24.

In various optional embodiments of the invention, a temperature sensor may also be disposed within ceramic body 24 (or elsewhere on the device).

FIG. 5 shows an embodiment of the invention as incorporated into a surgical device 60 (which may include a pair of tweezers or a forceps). Similar to the above described embodiment, opposing arms 20 and 40 are provided. Either or both of opposing arms 20 and 40 are moveable so as to grasp tissue therebetween.

Arm 20 comprises heating assembly 22 that is made from a ceramic body 24 and a metalized portion 26, as described above. Similarly, arm 40 may be covered with, or include, a compliant working surface for grasping tissue. Such compliant material may be a block 41 of silicone rubber, but is not so limited.

Ceramic body 24 on arm 40 in FIG. 5 may optionally be formed by flame spraying ceramic material onto a metal member (which may optionally comprise stainless steel). Thereafter, metalized portion 26 can be formed onto ceramic body 24 using any of the above-described methods.

What is claimed is:

1. A tissue cutting and sealing device, comprising:
   a pair of opposing elements dimensioned to grasp tissue therebetween; and
   a ceramic-metallic heating assembly on at least one of the opposing elements, wherein the ceramic-metallic heating assembly comprises:
     a ceramic body; and
     a metalized portion of the ceramic body extending in a longitudinal direction along an upper surface of the ceramic body, wherein the upper surface of the ceramic body is curved such that a center of the ceramic body is raised with respect to side edges of the ceramic body, and wherein the metalized portion of the ceramic body sticks upwardly from the upper surface of the ceramic body such that a top surface of the metallic portion protrudes above a topmost surface of the ceramic body, and wherein the ceramic body has a generally crescent-shaped cross section transverse to the longitudinal direction and defining an air gap between the ceramic body and an inner surface of said at least one of the opposing elements such that passing of heat from the ceramic body to the heating assembly is avoided.

2. The device of claim 1, wherein the metalized portion is formed integral to the ceramic body.

3. The device of claim 2, wherein the metalized portion is formed onto the ceramic body by a brazing process.

4. The device of claim 1, wherein the ceramic body is formed by a ceramic injection molding process, or a pressed ceramic molding.

5. The device of claim 1, wherein the ceramic body is dimensioned wide enough such that a tissue cutting zone forms adjacent to the metalized portion and a tissue sealing zone forms on either side of the cutting zone adjacent to a top surface of the ceramic body.

6. The device of claim 5, wherein the cutting zone forms where the metalized portion contacts the tissue and the sealing zones form where the ceramic body contacts the tissue.

7. The device of claim 1, wherein the metalized portion comprises at least one of the materials selected from the group consisting of titanium, zirconium, niobium, vanadium, nickel or molybdenum.

8. The device of claim 1, wherein the ceramic body comprises zirconia or alumina ceramic.

9. The device of claim 1, wherein one of the opposing elements is moveable and the other of the opposing elements is stationary, and wherein the at least one heating assembly is only mounted on the stationary opposing element.

10. The device of claim 9, wherein the moveable element comprises a compliant working surface for grasping tissue.

11. The device of claim 1, further comprising: a surgical device main body, wherein the pair of opposing elements are disposed at a distal end of the surgical device main body.

12. The device of claim 11, wherein the at least one heating assembly is disposed in an extended portion of the surgical device main body.

13. The device of claim 12, further comprising: a pin passing through the distal end of the heating assembly, wherein the pin completes a circuit between the metalized portion and a portion of the surgical device main body.

14. The device of claim 13, wherein the circuit is completed by current passing through the metalized portion of the ceramic-metallic heating assembly.

15. The device of claim 1, further comprising: a temperature sensor disposed within the ceramic body.

16. The device of claim 1, wherein the pair of opposing elements comprise a pair of surgical tweezers.

17. The device of claim 1, wherein the ceramic body is formed by flame spraying ceramic material onto a metal member.

18. The device of claim 1, wherein the ceramic-metallic heating assembly is a resistance heating system heated by a current passing therethrough.

19. The device of claim 1, wherein the ceramic body has a concave upper surface.

20. A tissue cutting and sealing device, comprising:
    a pair of opposing elements dimensioned to grasp tissue therebetween; and
    a ceramic-metallic heating assembly on at least one of the opposing elements, wherein the ceramic-metallic heating assembly comprises:
      a ceramic body;
      a metalized portion of the ceramic body extending in a longitudinal direction along an upper surface of the ceramic body, wherein the metalized portion of the ceramic body sticks upwardly from a topmost surface of the ceramic body, and wherein the ceramic body has a generally crescent-shaped cross section transverse to the longitudinal direction and defining an air gap between the ceramic body and an inner surface of said at least one of the opposing elements such that passing of heat from the ceramic body to the heating assembly is avoided; and
      a surgical device main body, wherein the pair of opposing elements are disposed at a distal end of the surgical device main body, wherein the at least one heating assembly is disposed in an extended portion of the surgical device main body, and wherein a bottom surface of the ceramic body is curved such that only the edges of the bottom surface of the ceramic body contact the extended portion of the surgical device main body.

21. The device of claim 20, wherein the ceramic body has a concave upper surface.

* * * * *